United States Patent [19]

Dillon

[11] Patent Number: 4,859,383

[45] Date of Patent: Aug. 22, 1989

[54] PROCESS OF PRODUCING A COMPOSITE MACROSTRUCTURE OF ORGANIC AND INORGANIC MATERIALS

[75] Inventor: Mark E. Dillon, Watertown, Mass.

[73] Assignee: Bio Med Sciences, Inc., Amherst, N.Y.

[21] Appl. No.: 185,424

[22] Filed: Apr. 25, 1988

Related U.S. Application Data

[62] Division of Ser. No. 56,386, Jun. 1, 1987.

[51] Int. Cl.$^4$ .......................... B28C 3/00; B29C 71/00
[52] U.S. Cl. ........................ 264/43; 264/49; 264/127; 264/233; 264/344
[58] Field of Search ............... 264/42, 43, 49, 127, 264/56, 60, 344, 233; 366/101, 106, 107

[56] References Cited

U.S. PATENT DOCUMENTS

| | | | |
|---|---|---|---|
| 2,728,698 | 12/1955 | Rudner | 264/49 |
| 2,782,180 | 2/1957 | Weidman | 264/127 X |
| 2,887,526 | 5/1959 | Rudner | 264/127 X |
| 3,047,275 | 7/1962 | Cox | 366/101 |
| 3,054,761 | 9/1962 | Moore et al. | 264/49 X |
| 3,179,378 | 4/1965 | Zenz et al. | 366/106 |
| 3,556,161 | 1/1971 | Roberts | 264/49 X |
| 3,700,380 | 10/1972 | Kitrilakis | 264/49 X |
| 3,843,570 | 10/1974 | Murayama | 264/49 X |
| 3,864,124 | 2/1975 | Breton et al. | 264/127 X |
| 3,992,725 | 11/1976 | Homsy | 264/56 X |
| 4,003,818 | 1/1977 | Juillard et al | 264/49 X |
| 4,007,969 | 2/1977 | Aubin et al. | 366/101 X |
| 4,049,589 | 9/1977 | Sakane | 264/49 X |
| 4,110,392 | 8/1978 | Yamazaki | 264/127 |
| 4,129,470 | 12/1978 | Honsy | 264/45.3 X |
| 4,256,845 | 3/1981 | Morris et al. | 264/49 X |
| 4,312,821 | 1/1982 | Jarcho et al. | 264/43 |
| 4,326,810 | 4/1982 | Schofield et al. | 366/106 |
| 4,406,410 | 9/1983 | Larson et al. | 366/101 X |
| 4,486,101 | 12/1984 | Brar | 366/101 |

FOREIGN PATENT DOCUMENTS 583418  12/1946  United Kingdom .............. 264/127

Primary Examiner—Jan H. Silbaugh
Assistant Examiner—Karen D. Kutach
Attorney, Agent, or Firm—Paul & Paul

[57] ABSTRACT

A composite self-supporting flexible agglomerated macrostructure is described which includes (1) a matrix of unfibrillated polytetrafluoroethylene resin and addition curable silicone and (2) particulate material including hydroxyapatite and/or tricalcium phosphate uniformly distributed throughout said matrix, the macrostructure being uniformly permeated by a network of open pores formed in the process of manufacture by intimately blending particulate sodium chloride and subsequently leaching the sodium chloride particles.

4 Claims, No Drawings

PROCESS OF PRODUCING A COMPOSITE MACROSTRUCTURE OF ORGANIC AND INORGANIC MATERIALS

CROSS REFERENCE TO RELATED APPLICATION

This application is a a divisional of U.S. patent application Ser. No. 056,386, filed June 1, 1987.

This invention relates to the field of biomaterials, more particularly to the field of bioceramic materials and most particularly to the field of composites of ceramic and organic biomaterials.

A biomaterial is a substance designed for implantation within or incorporation with a living system, which includes for example anything that is intermittently or continuously exposed to body fluids although they may actually be located outside of the body proper.

Biomaterials in the form of surgical implants have been manufactured from metals, plastic, rubber, textiles, ceramics and certain composites thereof. Since bioceramic materials can exist in either inert, surface-active or resorbable forms, the uses of such materials are manifold, such as for example artificial heart valves, knee and hip joint prostheses, alveolar ridge reconstructions, tooth/root implants, percutaneous access devices, bone plates and artificial tendons. Inert bioceramic materials are used for heart valves and electronic implants, for example, where durability, impermeability and lack of physiological response are needed. The term "inert" refers to materials that are essentially stable with little or no tissue reactivity when implanted within the living organism. Surface-active bioceramic materials possess chemical reactivity with the physiological environment. As healing of the incision or wound site occurs, a simultaneous chemical bond between the tissue and the implant surface is stimulated. For example, bone will bond to dense hydroxyapatite (HA). Resorbable bioceramic materials are temporary space fillers or scaffolds for new tissue to develop. Natural tissue reconstruction occurs simultaneously with resorption. For example, tricalcium phosphate (TCP), having the formula $Ca_3(PO_4)_2$ is biocompatible, has the ability to promote the ingrowth of soft tissue and bone, especially in the porous state, and is bioresorbable.

Sintered polytetrafluoroethylene (PTFE) has been used as a biomaterial in various forms, such as sutures and solid implants. PTFE biomaterials are desirable because of their low density, minimal time-dependent degradation characteristics, minimal deterioration in vivo, ease of shaping, pliability and ability to be dry sterilized. There are no antibody or thrombogenic reactions around PTFE implant sites.

Medical-grade silicone rubber is a known biomaterial which when vulcanized is resilient, easily fabricated, physiologically inert, capable of being dry sterilized and has low modulii of elasticity.

Biomaterials are disclosed in U.S. Pat. Nos. 3,992,725 and 4,129,470, which are porous reinforced structures comprising stainless steel, vitreous carbon, alumina, zirconia, or other ceramic fibers bonded together by "sintered" polytetrafluoroethylene. The exposed surfaces of this material are said to have sufficiently high surface tension to be highly blood wettable and therefore suitable for ingrowth of tissues.

It is an object of this invention to provide a composite of disparate biomaterials that is self-supporting without the necessity of fibrous or fibrillated reinforcement.

It is a further object of this invention to provide a composite of organic and inorganic biomaterials wherein the organic biomaterial constitutes a matrix throughout which the inorganic biomaterial is uniformly distributed.

It is a further object of this invention to provide a composite of disparate biomaterials that is self-supporting without the necessity of fibrous or fibrillated reinforcement and which contains open pores.

I have now discovered a self-supporting, porous flexible composite of known organic and inorganic biomaterials that does not depend upon fibrous or fibrillated materials for reinforcement. The present self-supporting composite can be readily shaped by molding, carving or abrading into sized products which embody the corresponding properties of the component biomaterials.

The composite composition of this invention is a self supporting flexible agglomerated macrostructure comprising (1) a matrix consisting essentially of a blend of sintered unfibrillated polytetrafluoroethylene resin and an addition cured silicone, said blend having been heated sufficiently to sinter the polytetrafluoroethylene and to cure said silicone composition; and (2) a particulate material selected from the class consisting of hydroxyapatite and tricalcium phosphate, said particulate material having a maximum size of about 2,000 microns, and being uniformly distributed throughout said matrix; said macrostructure being uniformly permeated by a network of open pores.

The process of manufacturing the composite material of this invention comprises the steps of (1) intimately blending a mixture of a major amount of unsintered and unfibrillated particulate polytetrafluoroethylene resin and minor amounts of (A) a hydrocarbon liquid and (B) an addition curable silicone composition containing a crosslinking catalyst, (2) intimately blending with the product of step (1) both (a) a particulate ceramic material selected from the group consisting of hydroxyapatite and tricalcium phosphate and (b) particulate sodium chloride whose particle size is determined by a desired size of open pores in the macrostructure, (3) introducing the product of step (2) into opposing streams of air within a mill so as to form a homogeneous particulate mixture, (4) subjecting the product of step (3) to mechanical pressure, (5) while maintaining pressure subjecting the product of step (4) to a temperature sufficient to sinter polytetrafluoroethylene and to cure said silicone composition, and (6) solubilizing the particulate sodium chloride so as to create a network of open pores in the product of step (5) corresponding in size to the original sodium chloride particles. The particulate sodium chloride particles may have a maximum particle size of about 2,000 microns.

DESCRIPTION OF THE PREFERRED EMBODIMENTS

EXAMPLE 1

29.44 grams (9.11 cc) of hydroxy apatite (calcium phosphate-tribasic - Fisher Scientific Company) powder was fired at 1200° C. for 4 hours, then ground and sifted to a particle size distribution of:
25% between 180 and 250 microns
25% between 90 and 180 microns
25% between 53 and 90 microns 25% below 53 microns 1.51 grams (0.479 cc) of tricalcium phosphate was synthesized by the following series of reactions: (confirmed by X-ray diffraction analysis)

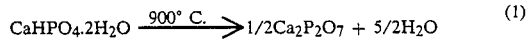

$$CaHPO_4 \cdot 2H_2O \xrightarrow{900° C.} 1/2 Ca_2P_2O_7 + 5/2 H_2O \quad (1)$$

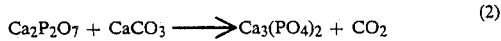

$$Ca_2P_2O_7 + CaCO_3 \longrightarrow Ca_3(PO_4)_2 + CO_2 \quad (2)$$

51.92 grams (23.98 cc) of sodium chloride (biological grade - Fisher Scientific Company) was ground and sifted to a particle size distribution of:
25% between 180 and 250 microns
50% between 90 and 180 microns
25% between 53 and 90 microns 3.28 grams (2.88 cc) of SILASTIC ® MDX4-4210 addition curable silicone elastomer (Dow Corning Corporation) was mixed into 3.64 grams (4.60 cc) of kerosene (Fisher Scientific Company) using a high sheer blender. The silicone ingredients comprised a 10/1 ratio of base to catalyst. The resultant solution was then slowly added to 25.30 grams (11.5 cc) of molding grade TEFLON ® 7A polytetrafluoroethylene (E. I. Dupont de Nemours and Company, Inc.) and jar tumbled for 8 hours. The hydroxy apatite, tricalcium phosphate and sodium chloride particulates were then added and the mixture tumbled for an additional 4 hours. The resultant blend of inorganic and organic materials was then introduced into an operating Trost Air Mill at 40 psi air pressure. This mill utilizes opposing jets of air to cause the material to impact against itself. At this air pressure, little or no size reduction of the particulate matter occurs. Within a period of two hours (to prevent curing of the silicone resin), the air-milled mixture was pressed between plates in a cylindrical die about two inches deep and 2.5 inches in diameter at room temperature to about 5,000 psi pressure. This pressed form was then hot pressed at 340° C. and 2,000 psi to "sinter" the polytetrafluoroethylene and cure (vulcanize) the silicone elastomer. After cooling, the hot pressed material was submerged in a reservoir of distilled water to dissolve the sodium chloride component particulates, thereby creating a network of open pores with a size distribution corresponding to that of the original salt crystals. The leaching treatment was performed over a period of 48 hours while maintaining a water solution rich in $Ca^{++}$ and $PO_4^{---}$ ions in order to inhibit dissolution of the tricalcium phosphate component. Finally, the leached composite material was dried at a temperature below 100° C.

The product produced by the procedure of Example 1 was in the form of a cylindrical disc with smooth exterior surfaces. The 2.5 inch disc is pliable and resilient in the hands. Extreme tearing force applied by hand causes jagged disruption of the composite with the exposed broken internal edges having a homogeneous appearance.

The proportions of the starting materials utilized in Example 1 were chosen to effect a final composition of 60 volume percent organic materials and 40 volume percent ceramic materials, with an overall porosity of 50 volume percent. The open pores may have a maximum dimension of about 2,000 microns. The ceramic phase is 5 volume percent tricalcium phosphate and 95 volume percent apatite. The organic phase is 20 volume percent silicone rubber and 80 volume percent polytetrafluoroethylene.

Polytetrafluoroethylene (PTFE) in its virgin resin state is on the order of 95 percent crystalline, unless it has been "sintered". The word "sintered" is used in this application to describe the action of heating PTFE above its crystalline melting point and then cooling it. Because of its extremely high melt viscosity, the molten PTFE retains some of its amorphous structure when quenched. This creates a condition known as "amorphous locking" which promotes dimensional and chemical stability. This invention however does not involve the well-known processes of solid state sintering or vitreous sintering. Therefore, the bioceramic materials utilized in accordance with the composite of this invention remain particulate within the organic matrix formed by the "sintered" PTFE and the cured (vulcanized) silicone elastomer.

Having thus described my invention, I claim:

1. A process of producing a composite macrostructure comprising the steps of first (1) intimately blending a mixture of a major amount of unsintered and unfibrillated particulate polytetrafluoroethylene resin and minor amounts of (A) a hydrocarbon liquid and (B) an addition curable silicone composition containing a crosslinking catalyst, then (2) intimately blending with the product of step (1) both a particulate ceramic material selected from the group consisting of hydroxyapatite and tricalcium phosphate and a particulate sodium chloride whose particle size is determined by a desired size of open pores in the macrostructure, then (3) introducing the product of step (2) into opposing streams of air within a mill so as to form a homogeneous particulate mixture, then (4) subjecting the product of step (3) to mechanical pressure within a die, then (5) hot pressing the product of step (4) at a temperature sufficient to sinter the polytetrafluoroethylene and to cure the silicone composition and then (6) solubilizing the particulate sodium chloride so as to create a network of open pores in the product of step (6) corresponding in size to the original sodium chloride particles.

2. The process of claim 1, wherein the pressure of step (4) is about 5,000 psi.

3. The process of claim 1, wherein the pressure of step (5) is 2,000 psi.

4. The process of claim 1, wherein the temperature of step (5) is 340° C.

* * * * *

UNITED STATES PATENT AND TRADEMARK OFFICE
CERTIFICATE OF CORRECTION

PATENT NO. : 4,859,383

DATED : August 22, 1989

INVENTOR(S) : Mark E. Dillon

It is certified that error appears in the above-identified patent and that said Letters Patent is hereby corrected as shown below:

Col. 4, claim 1, line 50, "product of step (6)" should be --product of step (5)--.

Signed and Sealed this

Thirty-first Day of July, 1990

*Attest:*

HARRY F. MANBECK, JR.

*Attesting Officer*  *Commissioner of Patents and Trademarks*